United States Patent [19]

Van Gemert et al.

[11] Patent Number: 5,578,252
[45] Date of Patent: Nov. 26, 1996

[54] PHOTOCHROMIC SUBSTITUTED NAPHTHOPYRAN COMPOUNDS

[75] Inventors: Barry Van Gemert, Murrysville; Anil Kumar, Pittsburgh, both of Pa.

[73] Assignee: Transitions Optical, Inc., Pinellas Park, Fla.

[21] Appl. No.: 564,547

[22] Filed: Nov. 29, 1995

Related U.S. Application Data

[60] Continuation-in-part of Ser. No. 454,784, May 31, 1995, which is a division of Ser. No. 80,246, Jun. 21, 1993, Pat. No. 5,466,398.

[51] Int. Cl.⁶ ........................... G02B 5/23; C07D 311/92
[52] U.S. Cl. ........................ 252/586; 549/389; 549/43; 549/44; 549/48; 549/365; 549/366; 546/196; 548/454
[58] Field of Search .................. 252/586; 549/389, 549/43, 44, 48, 365, 366; 548/454; 546/196

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,451,344 | 9/1995 | Knowles et al. | 252/586 |
| 5,466,398 | 11/1995 | Van Gemert et al. | 252/586 |

FOREIGN PATENT DOCUMENTS 816719  8/1937  France .

OTHER PUBLICATIONS

George A. Olah, *Friedel–Crafts and Related Reactions*, Interscience Publishers, vol. 3, Chap. XXXI, pp. 1–8, 82–88, 1964.

"1, 8, 17, 24–Tetroxa[8.8](2,6)naphthalenophane–3, 5, 19, 21–tetrayne–10, 30–dicarboxylic Acid Derivatives, Novel Complexors of Aromatic Guests, Esa T. Jarvi et al", J. Am Chem. Soc. 1982, 104, 7196–7204.

*Primary Examiner*—Philip Tucker
*Attorney, Agent, or Firm*—Frank P. Mallak; Irwin M. Stein

[57] ABSTRACT

Described are novel reversible photochromic 3H-naphtho[2,1-b]pyran compounds, examples of which are substituted with an oxy-bearing substituent at the number 8 carbon atom and with either an alkyl group at the number 7 carbon atom or with a carbonyl bearing substituent at the number 9 carbon atom and certain substituents at the 3-position of the pyran ring, e.g., 3,3-spirofluoren-9-ylidene 8-methoxy-9-carbomethoxy-3H-naphtho[2,1-b]pyran. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indoline) type compounds, are also described.

20 Claims, No Drawings

PHOTOCHROMIC SUBSTITUTED NAPHTHOPYRAN COMPOUNDS

CROSS REFERENCE TO RELATED APPLICATIONS

This application is a continuation-in-part of application Ser. No. 08/454,784 filed May 31, 1995 now pending, which is a division of application Ser. No. 08/080,246 filed Jun. 21, 1993, now U.S. Pat. No. 5,466,398.

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about –30° C. Irradiation of these compounds with visible light or upon raising the temperature to above about 0° C. is reported to reverse the coloration to a colorless state.

The present invention relates to novel 3H-naphtho[2,1-b] pyran compounds having certain substituents at the number 8 carbon atom and certain substituents either at the number 7 or number 9 carbon atom of the naphthopyran. These compounds are expected to have an improved solar response and an unexpectedly higher activating wavelength than corresponding compounds having no substituents on the naphtho portion of the naphthopyran or a substituent at the number 8 carbon atom. As discussed later, the number 7, 8 and 9 carbon atoms of 3H-naphtho[2,1-b]pyran compounds are part of the naphtho portion of the naphthopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Photochromic compounds useful in optical applications, such as conventional ophthalmic lenses, are those which possess (a) a high quantum efficiency for coloring in the near ultraviolet, (b) a low quantum yield for bleaching with white light, and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for ophthalmic and plano lenses when such materials have applied to or incorporated therein such photochromic compounds.

Another factor regarding the selection of potential photochromic compounds for optical applications is their response under a variety of solar conditions, e.g., a full mid-day sun, or the more highly filtered solar rays found early or late in the day. Ideally, photochromic compounds respond equally well under these differing conditions. Such a variety of solar conditions can be simulated on an optical bench with a Xenon lamp fitted with either a 320 nanometer or a 360 nanometer cutoff filter. Preferred photochromic compounds are those that have a minimal difference in optical density after exposure to both wavelength ranges of ultraviolet light. The ultraviolet light having a wavelength higher than 360 nanometer represents low light conditions that occur early or late in the day when the shorter wavelength components of the UV spectrum are attenuated.

The compounds of the present invention may be described as 3H-naphtho[2,1-b]pyrans that are substituted with an oxy-bearing substituent at the number 8 carbon atom and with either an alkyl group at the number 7 carbon atom or with a carbonyl bearing substituent at the number 9 carbon atom. In addition, these compounds have certain substituents at the 3 position of the pyran ring. These naphthopyran compounds may be represented by the following graphic formula I:

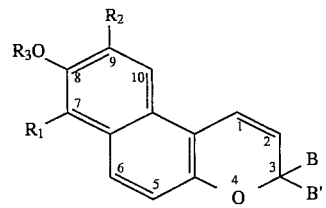

In graphic formula I, $R_1$ may be hydrogen or a $C_1$–$C_6$ alkyl, e.g., methyl, ethyl, propyl, n-butyl, iso-butyl, n-amyl, iso-amyl, hexyl, etc. Preferably, $R_1$ is hydrogen or a $C_1$–$C_5$ alkyl. More preferably, $R_1$ is hydrogen or a $C_1$–$C_4$ alkyl. Most preferably, $R_1$ is hydrogen or methyl. $R_2$ may be hydrogen or the group, 13 C(O)W, W being —$OR_4$ or -N($R_5$)$R_6$, wherein $R_4$ may be hydrogen, allyl, $C_1$–$C_6$ alkyl, e.g., methyl, ethyl, propyl, isopropyl, n-butyl, iso-butyl, sec-butyl, amyl, hexyl, etc., phenyl, $C_1$–$C_6$ monoalkyl substituted phenyl, e.g., tolyl, cumenyl, etc., $C_1$–$C_6$ monoalkoxy substituted phenyl, e.g., anisyl, ethoxyphenyl, etc., phenyl($C_1$–$C_3$)alkyl, e.g., benzyl, phenethyl, 3-phenylpropyl, etc., $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_2$–$C_4$)alkyl, $C_1$–$C_6$ monofluoroalkyl or $C_1$–$C_6$ monochloroalkyl, and wherein $R_5$ and $R_6$ each may be selected from the group consisting of hydrogen, $C_1$–$C_6$ alkyl, $C_5$–$C_7$ cycloalkyl, phenyl and mono- or di-substituted phenyl, or $R_5$ and $R_6$ together with the attached nitrogen atom form a mono- or di-substituted or unsubstituted heterocyclic ring selected from the group consisting of indolinyl, morpholino, piperidino, 1-pyrrolidyl, 1-pyrrolinyl, 1-imidazolidyl, 2-imidazolin-1-yl, 2-pyrazolidyl and 1-piperazinyl, said phenyl and heterocyclic ring substituents being selected from $C_1$–$C_6$ alkyl and $C_1$–$C_6$ alkoxy. Preferably, $R_2$ is hydrogen or the group, —C(O)W, W being -$OR_4$, wherein $R_4$ is allyl, $C_1$–$C_5$ alkyl or phenyl. More preferably, $R_4$ is allyl, $C_1$–$C_4$ alkyl or phenyl, most preferably, allyl, $C_1$–$C_3$ alkyl or phenyl. In graphic formula I, it is provided that one of $R_1$ and $R_2$ is hydrogen.

$R_3$ in graphic formula I may be hydrogen, $C_1$-$C_6$ alkyl, phenyl($C_1$-$C_3$)alkyl, $C_1$-$C_6$ monoalkyl substituted phenyl($C_1$-$C_3$)alkyl, $C_1$-$C_6$ monoalkoxy substituted phenyl($C_1$-$C_3$)alkyl, $C_1$-$C_6$ alkoxy($C_2$-$C_4$)alkyl, $C_5$-$C_7$ cycloalkyl, $C_1$-$C_4$ monoalkyl substituted $C_5$-$C_7$ cycloalkyl, $C_1$-$C_6$ monofluoroalkyl, $C_1$-$C_6$ monobromoalkyl, $C_1$-$C_6$ monochloroalkyl, allyl or the group, —C(O)X, wherein X may be $C_1$-$C_6$ alkyl, phenyl, $C_1$-$C_6$ mono- or $C_1$-$C_6$ di-alkyl substituted phenyl, $C_1$-$C_6$ mono- or $C_1$-$C_6$ di-alkoxy substituted phenyl, $C_1$-$C_6$ alkoxy, phenoxy, $C_1$-$C_6$ mono- or $C_1$-$C_6$ di-alkyl substituted phenoxy, $C_1$-$C_6$ mono- or $C_1$-$C_6$ di-alkoxy substituted phenoxy, $C_1$-$C_6$ alkylamino, phenylamino, $C_1$-$C_6$ mono- or $C_1$-$C_6$ di-alkyl substituted phenylamino, or $C_1$-$C_6$ mono- or $C_1$-$C_6$ di-alkoxy substituted phenylamino. Preferably, $R_3$ is hydrogen, $C_1$-$C_5$ alkyl, phenyl($C_1$-$C_3$)alkyl, or the group, —C(O)X, wherein X is a $C_1$-$C_5$ alkyl. More preferably, R is hydrogen, $C_1$-$C_3$ alkyl or the group, —C(O)X, wherein X is a $C_1$-$C_3$ alkyl. Most preferably, $R_3$ is hydrogen, methyl, or the group, —C(O)X, wherein X is methyl.

In graphic formula I, B is selected from the group consisting of the unsubstituted, mono-substituted, di-substituted, and tri-substituted aryl groups, phenyl and naphthyl. Preferably, B is represented by the following graphic formula II:

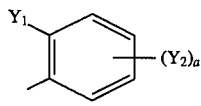

II wherein, $Y_1$ is selected from the group consisting of $C_1$-$C_5$ alkyl, $C_1$-$C_5$ alkoxy, fluoro, and chloro, each $Y_2$ is selected from the group consisting of $C_1$-$C_5$ alkyl, $C_1$-$C_5$ alkoxy, hydroxy, chloro, fluoro, acryloxy, and methacryloxy, and a is the integer 0, 1 or 2. More preferably, $Y_1$ is selected from the group consisting of $C_1$-$C_3$ alkyl, $C_1$-$C_3$ alkoxy and fluoro, each $Y_2$ is selected from the group consisting of $C_1$-$C_3$ alkyl and $C_1$-$C_3$ alkoxy, and a is the integer 0 or 1. Most preferably, $Y_1$ is selected from the group consisting of $C_1$-$C_2$ alkyl, $C_1$-$C_2$ alkoxy and fluoro, each $Y_2$ is selected from the group consisting of $C_1$-$C_2$ alkyl and $C_1$-$C_2$ alkoxy, and a is the integer 0 or 1.

B' in graphic formula I, may be selected from the group consisting of: (i) the unsubstituted, mono- and di-substituted aromatic heterocyclic groups dibenzothienyl, dibenzofuranyl and carbazolyl, each of said aryl substituents for B and said aromatic heterocyclic substituents described in this part for B' being selected from the group consisting of hydroxy, amino, mono($C_1$-$C_6$)alkylamino, di($C_1$-$C_6$)alkylamino, morpholino, piperidino, 1-indolinyl, pyrrolidyl, 1-imidazolidyl, 2-imidazolin-1-yl, 2-pyrazolidyl, pyrazolinyl, 1-piperazinyl, $C_1$-$C_6$ alkyl, $C_1$-$C_6$ fluoroalkyl, $C_1$-$C_6$chloroalkyl, $C_1$-$C_6$ alkoxy, mono($C_1$-$C_6$)alkoxy($C_1$-$C_4$)alkyl, acryloxy, methacryloxy, fluoro and chloro; (ii) the groups represented by the following graphic formulae II A and II B:

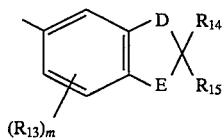

II A

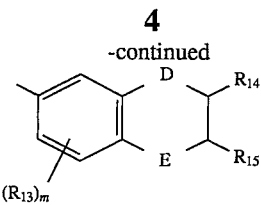

II B wherein D may be carbon or oxygen and E may be oxygen or substituted nitrogen, provided that when E is substituted nitrogen, D is carbon, said nitrogen substituent being selected from the group consisting of hydrogen, $C_1$-$C_6$ alkyl, and $C_2$-$C_6$ acyl, each $R_{13}$ may be $C_1$-$C_6$ alkyl, $C_1$-$C_6$ alkoxy, hydroxy, chloro or fluoro, $R_{14}$ and $R_{15}$ may each be hydrogen or $C_1$-$C_6$ alkyl, and m may be the integer 0, 1 or 2; (iii) $C_1$-$C_6$ alkyl, $C_1$-$C_6$ fluoroalkyl, $C_1$-$C_6$ chloroalkyl, $C_1$-$C_6$alkoxy($C_1$-$C_4$)alkyl, $C_3$-$C_6$ cycloalkyl, mono($C_1$-$C_6$) alkoxy ($C_3$-$C_6$)cycloalkyl, mono ($C_1$-$C_6$)alkyl($C_3$-$C_6$)cycloalkyl, fluoro($C_3$-$C_6$)cycloalkyl, and chloro($C_3$-$C_6$)cycloalkyl; and (iv) the group represented by the following graphic formula II C:

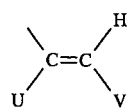

II C wherein U may be hydrogen or $C_1$-$C_4$ alkyl, and V may be selected from the unsubstituted, mono- and di-substituted members of the group consisting of naphthyl, phenyl, furanyl and thienyl, wherein each of the substituents for each member of said group may be $C_1$-$C_4$ alkyl, $C_1$-$C_4$ alkoxy, fluoro or chloro; or B and B' taken together may form fluoren-9-ylidene, mono- or di-substituted fluoren-9-ylidene or a member selected from the group consisting of saturated $C_3$-$C_{12}$ spiro-monocyclic hydrocarbon rings, saturated $C_7$-$C_{12}$ spiro-bicyclic hydrocarbon rings, and saturated $C_7$-$C_{12}$ spiro-tricyclic hydrocarbon rings, provided that B and B' do not form spiro-tricyclic adamantylidene, each of the fluoren-9-ylidene substituents being selected from the group consisting of $C_1$-$C_4$ alkyl, $C_1$-$C_4$ alkoxy, fluoro and chloro.

Preferably, B' is selected from the group consisting of: (i) the unsubstituted, mono- and di-substituted aromatic heterocyclic groups dibenzothienyl, dibenzofuranyl and carbazolyl, each of said aromatic heterocyclic substituents being selected from the group consisting of morpholino, piperidino, $C_1$-$C_4$ alkyl, $C_1$-$C_4$ alkoxy, fluoro and chloro; (ii) the groups represented by graphic formula II A, wherein D is carbon and E is oxygen, each $R_{13}$ is $C_1$-$C_4$ alkyl, $C_1$-$C_4$ alkoxy, hydroxy, chloro or fluoro, $R_{14}$ and $R_{15}$ are each hydrogen or $C_1$-$C_4$ alkyl, and m is the integer 0, 1 or 2; (iii) $C_1$-$C_4$ alkyl, $C_1$-$C_6$ alkoxy($C_1$-$C_4$)alkyl and $C_3$-$C_6$ cycloalkyl; and (iv) the group represented by graphic formula II C, wherein U is hydrogen or methyl, and V is phenyl or mono-substituted phenyl, said phenyl substituent being $C_1$-$C_4$ alkyl, $C_1$-$C_4$ alkoxy or fluoro; or B and B' taken together form fluoren-9-ylidene or mono-substituted fluoren-9-ylidene or a member selected from the group consisting of saturated $C_3$-$C_8$ spiromonocyclic hydrocarbon rings, saturated $C_7$-$C_{10}$ spiro-bicyclic hydrocarbon rings, and saturated $C_7$-$C_{10}$ spiro-tricyclic hydrocarbon rings, said fluoren-9-ylidene substituent being selected from the group consisting of $C_1$-$C_3$ alkyl, $C_1$-$C_3$ alkoxy and fluoro.

More preferably, B' is selected from the group consisting of: (i) the unsubstituted, mono- and di-substituted aromatic heterocyclic groups dibenzothienyl and dibenzofuranyl, each of said aromatic heterocyclic substituents being selected from the group consisting of morpholino, piperidino, $C_1$-$C_2$ alkyl and $C_1$-$C_2$ alkoxy; and (ii) the groups represented by graphic formula II A, wherein D is carbon and E is oxygen, each $R_{13}$ is $C_1$–$C_2$ alkyl, $C_1$–$C_2$ alkoxy or fluoro, $R_{14}$ and $R_{15}$ are each hydrogen or $C_1$–$C_2$ alkyl, and m is the integer 0, 1 or 2; or B and B' taken together form fluoren-9-ylidene, bornylidene, norbornylidene or bicyclo [3.3.1]nonan-9-ylidene. Most preferably, B' is dibenzofuran-2-yl, 2,3-dihydrobenzofuran-5-yl, fluoren-9-ylidene, norbornylidene or bicyclo[3.3.1]nonan-9-ylidene.

Compounds represented by graphic formula I may be prepared by the following steps in Reactions A through E. In Reactions A and B, benzophenones represented by graphic formula IV and IV A are either purchased or prepared by Friedel-Crafts methods using an appropriately substituted or unsubstituted benzoyl chloride of graphic formula IV and a commercially available substituted or unsubstituted B' group of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

The compounds represented by B' and graphic formulae III, in Reaction A, are dissolved in a solvent, such as carbon disulfide or methylene chloride, and reacted in the presence of a Lewis acid, such as aluminum chloride or tin tetrachloride, to form the corresponding substituted benzophenone represented by graphic formula IV (or IV A in Reaction B). R' represents potential phenyl substituents.

REACTION A

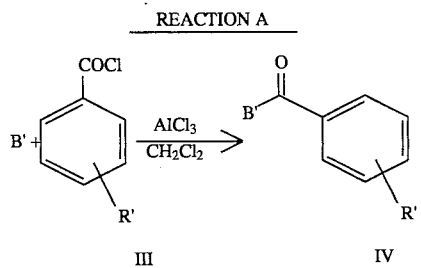

In Reaction B, the substituted or unsubstituted ketone represented by graphic formula IV A, in which B may represent a substituted or unsubstituted naphthalene, is reacted with sodium acetylide in a suitable solvent, such as anhydrous tetrahydrofuran (THF), to form the corresponding propargyl alcohol represented by graphic formula VI. Propargyl alcohols having B' groups representing a substituted or unsubstituted benzene or heteroaromatic compound may be prepared from commercially available ketones or ketones prepared, for example, via reaction of an acyl halide with a substituted or unsubstituted benzene or heteroaromatic compound. Propargyl alcohols having B' groups represented by graphic formula II C may be prepared by the methods described in U.S. Pat. No. 5,274,132, column 2, lines 40 to 68.

REACTION B

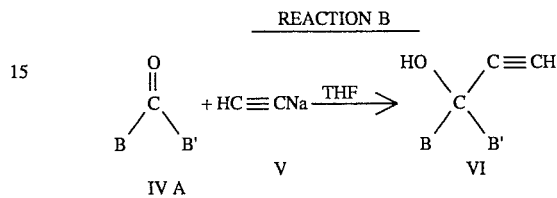

In Reaction C, the propargyl alcohol represented by graphic formula VI is coupled with a 7-substituted 2,6-naphthalene diol, represented by graphic formula VII, under acidic conditions to form the naphthopyran of graphic formula I A. 7-substituted 2,6-naphthalene diol e.g., 2,6-dihydroxy-7-carbomethoxynaphthalene, can be prepared by methods described for the synthesis of n-hexyl-3,7-dihydroxy-2-naphthoate described in the Journal of the American Chemical Society 104, pages 7196 to 7204, 1982.

In order to make the compound represented by graphic formula I B, it is necessary to derivatize, i.e., acylate, methylate, benzylate, etc . . ., the hydroxyl group on the number 8 carbon atom of the naphthopyran represented by graphic formula I A. This is accomplished by reaction of the hydroxyl group with an alkyl or aroyl halide, chloroformate, isocyanate, etc.

REACTION C

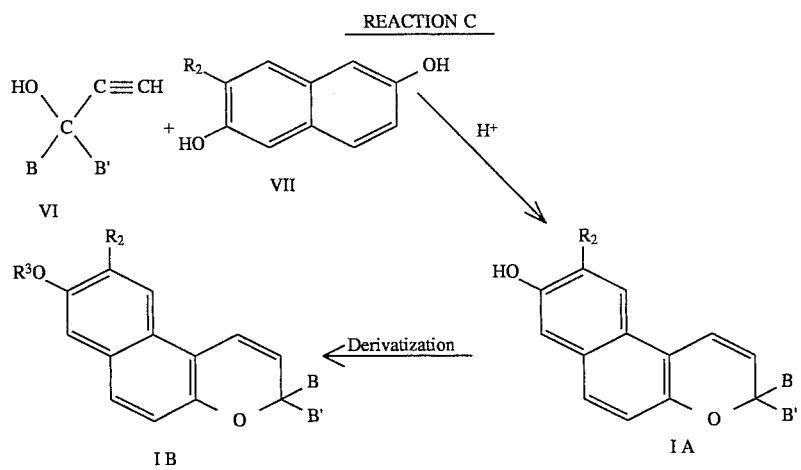

In Reaction D, the naphthaldehyde or alkyl aryl ketone represented by graphic formulae VIII and VIII A respectively, is reduced using the Wolff-Kishner process to yield the compound represented by graphic formula IX, which can be selectively brominated to yield the bromonaphthalene compound of graphic formula IX A. This compound may be subjected to high pressure copper mediated solvolysis to produce the substituted naphthol represented by graphic formula IX B followed by demethylation to produce the substituted naphthol represented by graphic formula VII A. The various compounds prepared in this series of reactions may be commercially available from fine chemical manufacturers or may be custom synthesized.

naphthopyran of graphic formula I C. The compound represented by graphic formula I D is produced by derivatizing the hydroxyl group on the number 8 carbon atom of the naphthopyran compound represented by graphic formula I C in an identical manner as previously discussed for Reaction C. If $R_3$ is methyl, the compound represented by graphic formula IX B in Reaction D may be used directly in place of the compound represented by VII A in Reaction E.

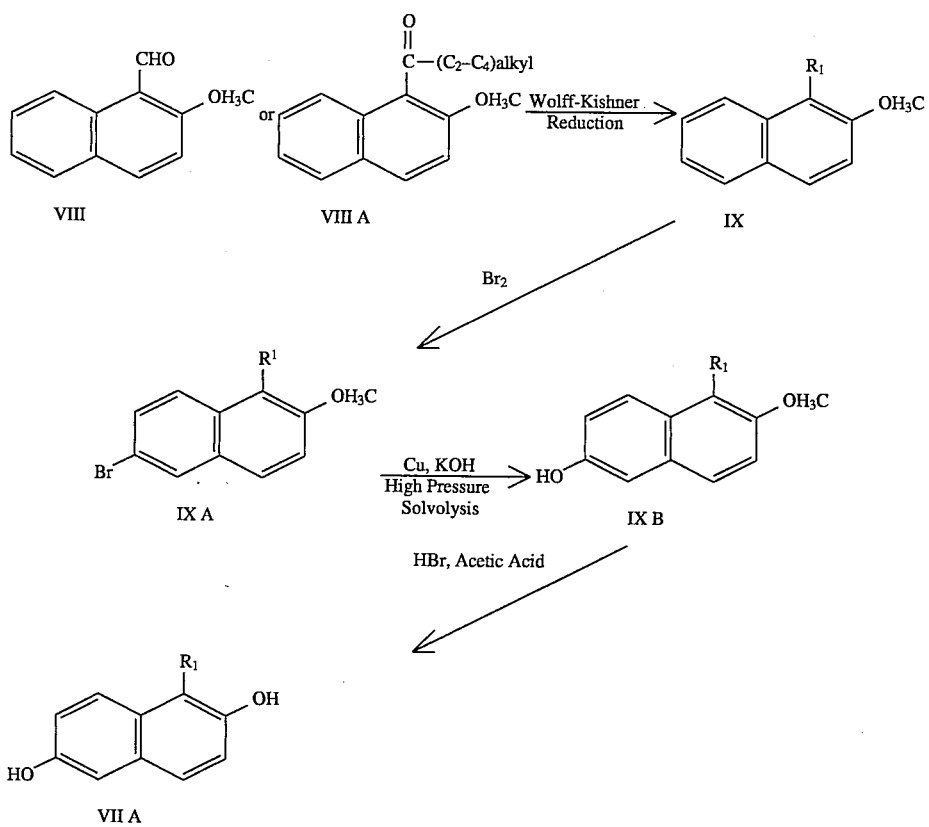

In Reaction E, the propargyl alcohol represented by graphic formula VI is coupled with a substituted naphthol of graphic formula VII A under acidic conditions to form the

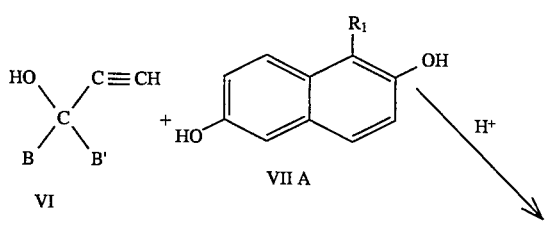

-continued
REACTION E

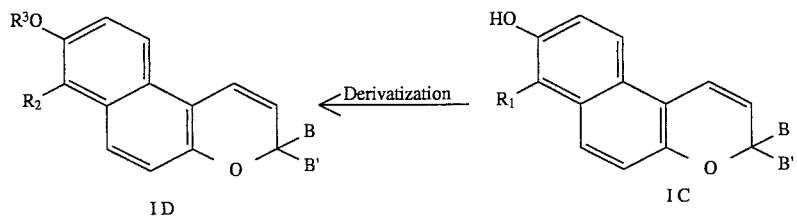

Compounds represented by graphic formulae I and I A through I D may be used in those applications in which organic photochromic substances may be employed, such as optical lenses, e.g., ophthalmic and plano lenses, face shields, goggles, ski goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I and I A through I D are expected to exhibit color changes from colorless to colors ranging from yellow to orange and red.

Examples of contemplated naphthopyrans within the scope of the invention are the following:

(a) 3-(4-methoxyphenyl)-3-(2-methyl-2,3- dihydrobenzofur-5-yl)-8-methoxy-9-carbomethoxy-3H-naphtho[2,1-b]pyran;

(b) 3-(4-methoxyphenyl)-3-(2-phenyl-1-methylvinyl)-8-acetoxy-9-carbomethoxy-3H-naphhtho [2,1-b]pyran;

(c) 3-(4-methoxyphenyl)-3-(9-ethylcarbozol-2-yl)-8-methoxy-9-carbomethoxy-3H-naphthho [2, 1-b]pyran; and (d) 3,3-spirofluoren-9-ylidene-8-methoxy-9-carbomethoxy-3H-naphtho[2,1-b]pyran.

It is contemplated that the organic photochromic naphthopyrans of graphic formulae I and I A through I D be used alone or in combination with other appropriate complementary organic photochromic materials so that together they produce a near neutral gray or brown color shade when a photochromic article, e.g. a plastic lens containing such photochromic materials, is exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than ophthalmic lenses.

Complementary photochromic compounds with which the novel naphthopyran compounds of the present invention may be used include organic photochromic compounds having at least one activated absorption maxima within the range of between about 400 and about 700 nanometers, or substances containing same, and may be incorporated, e.g., dissolved or dispersed, in a polymeric organic host material used to prepare photochromic articles and which compounds or mixtures of compounds color when activated to an appropriate hue.

All numbers used herein are to be understood as modified in all instances by the term "about".

A first group of complementary organic photochromic substances contemplated for use with the organic photochromic naphthopyrans of the present invention are those having an activated absorption maximum within the visible range of greater than about 570 nanometers, e.g., between about greater than 570 to 700 nanometers. These materials typically exhibit a blue, blueish-green, or blueish-purple color when exposed to ultraviolet light in an appropriate solvent or matrix. Many of such compounds are described in the open literature. Examples of such compounds are described in U.S. Pat. No. 5,458,814 column 9, lines 22 to 53.

A second group of complementary organic photochromic substances contemplated for use with the organic photochromic naphthopyrans of the present invention are those having at least one absorption maximum within the visible range of between about 400 and less than about 500 nanometers. These materials typically exhibit a yellow-orange color when exposed to ultraviolet light in an appropriate solvent or matrix. Such compounds include certain chromenes, i.e., benzopyrans and naphthopyrans. Many of such chromenes are described in the open literature, e.g., U.S. Pat. Nos. 3.,567,605; 4,826,977; and 5,066,818. Other examples of such compounds are described in U.S. Pat. No. 5,458,814 column 9, line 64 to column 10, line 19.

A third group of complementary organic photochromic substances contemplated for use with the organic photochromic naphthopyrans of the present invention are those having an absorption maximum within the visible range of between about 400 to about 500 nanometers and another absorption maximum within the visible range of between about 500 to about 700 nanometers. These materials typically exhibit color(s) ranging from yellow to purple and yellow/brown to purple/gray when exposed to ultraviolet light in an appropriate solvent or matrix. Examples of such compounds are described in U.S. Pat. No. 5,458,814 column 10, lines 20 to 44.

Photochromic articles of the present invention may contain one photochtromic compound or a mixture of photochromic compounds, as desired or required. Individual photochromic compounds or mixtures of photochromic compounds may be used to attain certain activated colors such as neutral grays or browns.

The compounds of the present invention (hereinafter also referred to and included as the second group photochromic compound) may be used also in combination with the organic photochromic substances of the first complementary group of photochromic compounds described herein, i.e., those that color to colors blue, blueish-green, or blueish-purple or with other organic photochromic substances in the aforesaid second group of photochromic compounds. Either members of the first or second group of photochromic compounds or mixtures of such compounds may be combined with or used in conjunction with the third group described herein that exhibit colors ranging from yellow to purple and yellow/brown to purple/gray.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): $x=0.260$ to $0.400$, $y=0.280$ to $0.400$ following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally, such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to aphotochromic optical host material may range from about 0.05 to about 1.0, e.g., from 0.1 to about 0.45, milligrams per square centimeter of surface to which the photochromic substance(s) is incorporated or applied. When mixtures of the aforedescribed organic photochromic complementary groups are used, the weight ratio of potential combinations of such groups, i.e., (first to second), (second to third), and (the naphthopyran of the present invention to other second group compounds) will vary from about 1:3 to about 3:1, e.g., between about 0.75:1 and about 2:1. The combination of the first, second, and third described organic photochromic complementary groups may have a weight ratio that will vary from about 1:3:1 to about 3:1:3.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, and alkoxylated polyhydric alcohol acrylate monomers such as ethoxylated trimethylol propane triacrylate monomers; polymers, i.e., homopolymers and copolymers, of polyfunctional, i.e., mono-, di-, tri-, tetra, or multi-functional, acrylate and/or methacrylate monomers, polyacrylates, polymethacrylates, poly($C_1$–$C_{12}$ alkyl methacrylates) such as poly(methyl methacrylate), polyoxy(alkylene methacrylates) such as poly(ethylene glycol bis methacrylates), poly(alkoxylated phenol methacrylates) such as poly(ethoxylated bisphenol A dimethacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile. More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66.

Although the present invention has been described with reference to the specific details of particular embodiments thereof, it is not intended that such details be regarded as limitations upon the scope of the invention except insofar as and to the extent that they are included in the accompanying claims.

What is claimed is:

1. A naphthopyran compound represented by the following graphic formula:

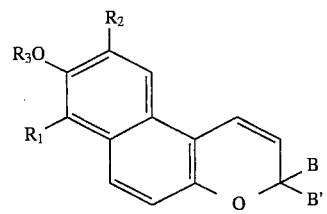

wherein:

(a) $R^1$ is hydrogen or a $C_1$–$C_6$ alkyl; $R_2$ is hydrogen or the group, —C(O)W, W being —$OR_4$ or —$N(R_5)R_6$, wherein $R_4$ is hydrogen, allyl, $C_1$–$C_6$ alkyl, phenyl, $C_1$–$C_6$ monoalkyl substituted phenyl, $C_1$–$C_6$ monoalkoxy substituted phenyl, phenyl($C_1$–$C_3$)alkyl, $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_2$–$C_4$)alkyl, $C_1$–$C_6$ monofluoroalkyl, or $C_1$–$C_6$ monochloroalkyl, and wherein $R_5$ and $R_6$ each are selected from the group consisting of hydrogen, $C_1$–$C_6$ alkyl, $C_5$–$C_7$ cycloalkyl, phenyl and mono- or di-substituted phenyl, or $R_5$ and $R_6$ together with the attached nitrogen atom form a mono- or di-substituted or unsubstituted heterocyclic ring selected from the group consisting of indolinyl, morpholino, piperidino, 1-pyrrolidyl, 1-pyrrolinyl, 1-imidazolidyl, 2-imidazolin-1-yl, 2-pyrazolidyl and 1-piperazinyl, said phenyl and heterocyclic ring substituents being selected from $C_1$–$C_6$ alkyl and $C_1$–$C_6$ alkoxy; $R_3$ is hydrogen, $C_1$–$C_6$ alkyl, phenyl($C_1$–$C_3$)alkyl, $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_1$–$C_4$)alkyl, $C_5$–$C_7$ cycloalkyl, $C_1$–$C_4$ monoalkyl substituted $C_5$–$C_7$ cycloalkyl, $C_1$–$C_6$ monofluoroalkyl, $C_1$–$C_6$ monobromoalkyl, $C_1$–$C_6$ monochloroalkyl, allyl or the group, —C(O)X, wherein X is $C_1$–$C_6$ alkyl, phenyl, $C_1$–$C_6$ mono- or $C_1$–$C_6$ di-alkyl substituted phenyl, $C_1$–$C_6$ mono- or $C_1$–$C_6$ di-alkoxy substituted phenyl, $C_1$–$C_6$ alkoxy, phenoxy, $C_1$–$C_6$ mono- or $C_1$–$C_6$ di-alkyl substituted phenoxy, $C_1$–$C_6$ mono- or $C_1$–$C_6$ di-alkoxy substituted phenoxy, $C_1$–$C_6$ alkylamino, phenylamino, $C_1$–$C_6$ mono- or $C_1$–$C_6$ di-alkyl substituted phenylamino, or $C_1$–$C_6$ mono- or $C_1$–$C_6$ di-alkoxy substituted phenylamino, provided that one of $R_1$ and $R_2$ is hydrogen; and (b) B is selected from the group consisting of the unsubstituted, mono-, di- and tri-substituted aryl groups, phenyl and naphthyl; and (c) B' is selected from the group consisting of:
(i) the unsubstituted, mono- and di-substituted aromatic heterocyclic groups dibenzothienyl, dibenzofuranyl, and carbazolyl, said aryl and aromatic heterocyclic substituents described in (b) and (c) being selected from the group consisting of hydroxy, amino, mono($C_1$–$C_6$)alkylamino, di($C_1$–$C_6$)alkylamino, morpholino, piperidino, 1-indolinyl, pyrrolidyl, 1-imidazolidyl, 2- imidazolin-1-yl, 2-pyrazolidyl, pyrazolinyl, 1-piperazinyl, $C_1$–$C_6$ alkyl, $C_1$–$C_6$ fluoroalkyl, $C_1$–$C_6$ chloroalkyl, $C_1$–$C_6$ alkoxy, mono($C_1$–$C_6$)alkoxy($C_1$–$C_4$)alkyl, acryloxy, methacryloxy, chloro and fluoro;

(ii) the groups represented by the following graphic formulae:

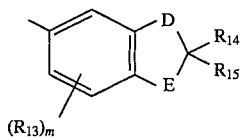

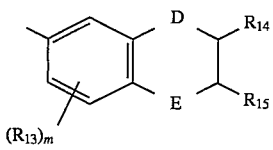

wherein D is carbon or oxygen and E is oxygen or substituted nitrogen, provided that when E is substituted nitrogen, D is carbon, said nitrogen substituent being selected from the group consisting of hydrogen, $C_1$–$C_6$ alkyl, and $C_2$–$C_6$ acyl, each $R_{13}$ is $C_1$–$C_6$ alkyl, $C_1$–$C_6$ alkoxy, hydroxy, chloro or fluoro, $R_{14}$ and $R_{15}$ are each hydrogen or $C_1$–$C_6$ alkyl, and m is the integer 0, 1 or 2;

(iii) $C_1$–$C_6$ alkyl, $C_1$–$C_6$ fluoroalkyl, $C_1$–$C_6$ chloroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$) cycloalkyl, fluoro($C_3$–$C_6$)cycloalkyl and chloro($C_3$–$C_6$) cycloalkyl; and (iv) the group represented by the following graphic formula:

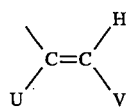

wherein U is hydrogen or $C_1$–$C_4$ alkyl, and V is selected from the unsubstituted, mono- and di-substituted members of the group consisting of naphthyl, phenyl, furanyl and thienyl, wherein the substituents for each member of said group are $C_1$–$C_4$ alkyl, $C_1$–$C_4$ alkoxy, fluoro or chloro; or (d) B and B' taken together form fluoren-9-ylidene, mono- or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, provided that B and B' do not form spiro-tricyclic adamantylidene, each of said fluoren-9-ylidene substituents being selected from the group consisting of $C_1$–$C_4$ alkyl, $C_1$–$C_4$ alkoxy, fluoro and chloro.

2. The naphthopyran of claim 1 wherein:

(a) $R_1$ is hydrogen or a $C_1$–$C_5$ alkyl; $R_2$ is hydrogen or the group, —C(O)W, W being —$OR_4$, wherein $R_4$ is allyl, $C_1$–$C_5$ alkyl or phenyl; $R_3$ is hydrogen, phenyl($C_1$–$C_3$)alkyl or the group, —C(O)X, wherein X is a $C_1$–$C_5$ alkyl, provided that either $R_1$ or $R_2$ is hydrogen;

(b) B is represented by the following graphic formulae:

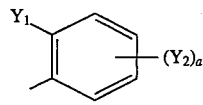

wherein, $Y_1$ is selected from the group consisting of $C_1$–$C_5$ alkyl, $C_1$–$C_5$ alkoxy, fluoro, and chloro, each $Y_2$ is selected from the group consisting of $C_1$–$C_5$ alkyl, $C_1$–$C_5$ alkoxy, hydroxy, chloro, fluoro, acryloxy, and methacryloxy, and a is the integer 0, 1 or 2; and (c) B' is selected from the group consisting of:
(i) the unsubstituted, mono- and di-substituted aromatic heterocyclic groups dibenzothienyl, dibenzofuranyl and carbazolyl, each of said aromatic heterocyclic substituents being selected from the group consisting of morpholino, piperidino, $C_1$–$C_4$ alkyl, $C_1$–$C_4$alkoxy, fluoro and chloro;
(ii) the groups represented by the following graphic formula:

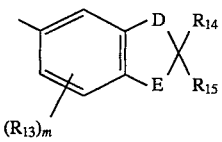

wherein D is carbon and E is oxygen; each $R_{13}$ is $C_1$–$C_4$ alkyl, $C_1$–$C_4$ alkoxy, hydroxy, chloro or fluoro, $R_{14}$ and $R_{15}$ are each hydrogen or $C_1$–$C_4$ alkyl, and m is the integer 0, 1 or 2;
(iii) $C_1$–$C_4$ alkyl, $C_1$–$C_6$ alkoxy($C_1$–$C_4$)alkyl and $C_4$–$C_6$ cycloalkyl; and
(iv) the group represented by the following graphic formula:

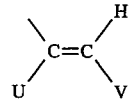

wherein U is hydrogen or methyl, and V is phenyl or mono-substituted phenyl, said phenyl substituent being $C_1$–$C_4$ alkyl, $C_1$–$C_4$ alkoxy or fluoro; or (d) B and B' taken together form fluoren-9-ylidene or mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from $C_1$–$C_3$ alkyl, $C_1$–$C_3$ alkoxy and fluoro.

3. The naphthopyran of claim 2 wherein:

(a) $R_1$ is hydrogen or $C_1$–$C_4$ alkyl; $R_2$ is hydrogen or the group, —C(O)W, W being —$OR_4$, wherein $R_4$ is allyl, phenyl or $C_1$–$C_4$ alkyl; and $R_3$ is hydrogen, $C_1$–$C_4$ alkyl, phenyl($C_1$–$C_3$)alkyl, or the group, —C(O)X wherein X is a $C_1$–$C_4$ alkyl;

(b) $Y_1$ is selected from the group consisting of $C_1$–$C_3$ alkyl, $C_1$–$C_3$ alkoxy and fluoro, each $Y_2$ is selected from the group consisting of $C_1$–$C_3$ alkyl and $C_1$–$C_3$ alkoxy, and a is the integer 0 or 1; and (c) B' is selected from the group consisting of:
(i) the unsubstituted, mono- and di-substituted aromatic heterocyclic groups dibenzothienyl and dibenzofuranyl, each of said aromatic heterocyclic substituents being selected from the group consisting of morpholino, piperidino, $C_1$–$C_2$ alkyl and $C_1$–$C_2$ alkoxy; and (ii) the groups represented by the following graphic formula:

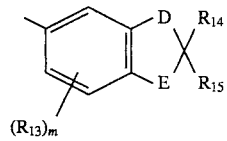

wherein D is carbon and E is oxygen, each $R_{13}$ is $C_1$–$C_2$ alkyl, $C_1$–$C_2$ alkoxy or fluoro, $R_{14}$ and $R_{15}$ are each hydrogen or $C_1$–$C_2$alkyl, and m is the integer 0, 1 or 2; or (d) B and B' taken together form fluoren-9-ylidene, bornylidene, norbornylidene or bicyclo[3.3.1]nonan-9-ylidene.

4. The naphthopyran of claim 3 wherein:

(a) $R_1$ is hydrogen or methyl; $R_2$ is hydrogen or the group, —C(O)W, W being —OR$_4$, wherein $R_4$ is allyl, $C_1$–$C_3$ alkyl or phenyl; and $R_3$ is hydrogen, methyl, or the group, —C(O)X wherein X is methyl;

(b) $Y_1$ is selected from the group consisting of $C_1$–$C_2$ alkyl, $C_1$–$C_2$ alkoxy and fluoro, each $Y_2$ is selected from the group consisting of $C_1$–$C_2$ alkyl and $C_1$–$C_2$ alkoxy, and a is the integer 0 or 1; and (c) B' is selected from the group consisting of dibenzofuran-2-yl, 2,3-dihydrobenzofuran-5-yl, fluoren-9-ylidene, norbornylidene or bicyclo[3.3.1]nonan-9-ylidene.

5. A naphthopyran compound selected from the group consisting of:

(a) 3-(4-methoxyphenyl)-3-(2-methyl-2,3-dihydrobenzofur-5-yl )-8-methoxy-9-carbomethoxy-3H-naphtho[2, 1-b]pyran;

(b) 3-(4-methoxyphenyl)-3-(2-phenyl-1-methylvinyl)8-acetoxy-9-carbomethoxy-3H-naphhtho[2,1-b]pyran;

(c) 3-(4-methoxyphenyl)-3-(9-ethylcarbozol-2-yl)-8-methoxy-9-carbomethoxy-3H-naphthho[2,1-b]pyran; and (d) 3,3-spirofluoren-9-ylidene-8-methoxy-9-carbomethoxy-3H-naphtho[2,1-b]pyran.

6. A photochromic article comprising a polymeric organic host material and a photochromic amount of a naphthopyran compound of claim 1.

7. The photochromic article of claim 6 wherein the polymeric organic host material is selected from the group consisting of polyacrylates, polymethacrylates, poly ($C_1$–$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

8. A photochromic article comprising a polymeric organic host material and a photochromic amount of a naphthopyran compound of claim 2.

9. The photochromic article of claim 8 wherein the polymeric organic host material is selected from the group consisting of polyacrylates, polymethacrylates, poly($C_1$–$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

10. The photochromic article of claim 9 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

11. The photochromic article of claim 10 wherein the photochromic compound is present in an amount of from about 0.05 to 1.0 milligram per square centimeter of organic host material surface to which the photochromic substance(s) is incorporated or applied.

12. The photochromic article of claim 11 wherein the article is a lens.

13. A photochromic article comprising a photochromic amount of the naphthopyran compound of claim 3 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

14. A photochromic article comprising a photochromic amount of the naphthopyran compound of claim 4 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of polyacrylates, polymethacrylates, poly($C_1$–$C_{12}$ alkyl methacrylates), polyoxy(alkylene methacrylates), poly(alkoxylatedphenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

17. The photochromic article of claim 15 wherein the organic photochromic compound (b) is selected from the group consisting of:

(a) organic photochromic substances having at least one absorption maximum in the visible range of between about 400 and less than about 500 nanometers;

(b) organic photochromic substances having an absorption maximum within the visible range of between about 400 and about 500 nanometers and another absorption maximum within the visible range of between about 500 and about 700 nanometers; and (c) organic photochromic substances having an activated absorption maxima in the visible range of greater than about 570 nanometers; and (d) mixtures of said organic photochromic substances.

18. The photochromic article of claim 17 wherein the organic photochromic compound (b) is an organic photochromic substances having an activated absorption maxima in the visible range of greater than 570 nanometers.

19. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

20. The photochromic article of claim 17 wherein the organic photochromic compound (b) is selected from the group consisting of spiro(indoline)naphthoxazines, spiro(indoline)-pyridobenzoxazines, spiro(benzindoline)pyridobenzoxazines, spiro(benzindoline)naphthoxazines, spiro(benzindoline)naphthopyrans, spiro(indoline) benzoxazines, spiro(indoline) benzopyrans, spiro(indoline)naphthopyrans, spiro(indoline) quinopyrans, spiro(indoline) pyrans, 3H-naphtho [2,1-b]pyrans, 2H-phenanthro[4,3 -b]pyrans; 3H-phenanthro[1,2-b]pyrans; benzopyran compounds and mixtures of such photochromic substances.

* * * * *

UNITED STATES PATENT AND TRADEMARK OFFICE
CERTIFICATE OF CORRECTION

PATENT NO. : 5,578,252
DATED : November 26, 1996
INVENTOR(S) : Barry Van Gemert et al It is certified that error appears in the above-indentified patent and that said Letters Patent is hereby corrected as shown below:

Column 14, claim 1, line 35,

"alkoxy($C_1$-$C_4$)alkyl" should be --alkoxy($C_2$-$C_4$)alkyl--

Signed and Sealed this

Fifth Day of January, 1999

Attest:

Attesting Officer

Acting Commissioner of Patents and Trademarks